US011779564B2

(12) United States Patent
Conte et al.

(10) Patent No.: US 11,779,564 B2
(45) Date of Patent: Oct. 10, 2023

(54) METHODS AND COMPOSITIONS FOR TREATING BILE ACID DIARRHEA, DIARRHEA ASSOCIATED WITH SMALL INTESTINE RESECTION OR GALLBLADDER REMOVAL, AND SHORT BOWEL SYNDROME

(71) Applicant: NAPO PHARMACEUTICALS, INC., San Francisco, CA (US)

(72) Inventors: Lisa A. Conte, San Francisco, CA (US); Pravin R. Chaturvedi, Andover, MA (US); Charles Conte, Manhasset, NY (US)

(73) Assignee: NAPO PHARMACEUTICALS, INC., San Francisco, CA (US)

( * ) Notice: Subject to any disclaimer, the term of this patent is extended or adjusted under 35 U.S.C. 154(b) by 168 days.

(21) Appl. No.: 16/617,466

(22) PCT Filed: May 31, 2018

(86) PCT No.: PCT/US2018/035471
§ 371 (c)(1),
(2) Date: Nov. 26, 2019

(87) PCT Pub. No.: WO2018/222921
PCT Pub. Date: Dec. 6, 2018

(65) Prior Publication Data
US 2020/0121636 A1     Apr. 23, 2020

Related U.S. Application Data

(60) Provisional application No. 62/513,257, filed on May 31, 2017.

(51) Int. Cl.
| | | |
|---|---|---|
| A61K 31/353 | (2006.01) | |
| A61P 1/12 | (2006.01) | |
| A61K 31/451 | (2006.01) | |
| A61K 36/47 | (2006.01) | |

(52) U.S. Cl.
CPC .......... *A61K 31/353* (2013.01); *A61K 31/451* (2013.01); *A61K 36/47* (2013.01); *A61P 1/12* (2018.01)

(58) Field of Classification Search
CPC ....................................................... A61P 1/12
See application file for complete search history.

(56) References Cited

U.S. PATENT DOCUMENTS

| | | | |
|---|---|---|---|
| 7,235,573 B2 | 6/2007 | Verkman et al. | |
| 7,323,195 B2 | 1/2008 | Rozhon et al. | |
| 7,341,744 B1 | 3/2008 | Rozhon et al. | |
| 7,638,543 B2 | 12/2009 | Verman et al. | |
| 7,700,093 B2 | 4/2010 | Farmer et al. | |
| 8,377,876 B2 | 2/2013 | Brand et al. | |
| 8,574,634 B2 | 11/2013 | Rozhon et al. | |
| 8,846,113 B2 | 9/2014 | Quart et al. | |
| 8,962,680 B2 | 2/2015 | Forbes et al. | |
| 9,585,868 B2 | 3/2017 | Forbes et al. | |
| 9,980,938 B2 | 5/2018 | Quart et al. | |
| 2012/0202876 A1 | 8/2012 | Verkman et al. | |
| 2014/0011869 A1 | 1/2014 | Rozhon et al. | |
| 2014/0134206 A1 | 5/2014 | Kahoo et al. | |
| 2016/0045565 A1 | 2/2016 | Ling et al. | |
| 2020/0108047 A1 | 4/2020 | Conte et al. | |
| 2020/0121636 A1 | 4/2020 | Conte et al. | |
| 2020/0345687 A1 | 11/2020 | Conte | |

FOREIGN PATENT DOCUMENTS

| | | | | |
|---|---|---|---|---|
| JP | 2009534323 P | 9/2009 | | |
| WO | WO-2011044167 A1 * | 4/2011 | ............... | A61P 1/04 |
| WO | 2017112953 A1 | 6/2017 | | |
| WO | 2017127710 A1 | 7/2017 | | |
| WO | 2019180688 A1 | 9/2019 | | |

OTHER PUBLICATIONS

PARRISH: "The Clinician's Guide to Short Bowel Syndrome, Nutrition Issues in Gastroenterology, Series #31", Practical Gastroenterology, Sep. 2005 (Sep. 1, 2005), pp. 67-104, 106*.
International Search Report and Written Opinion issued in PCT/US2018/035471, dated Aug. 7, 2018, 12 pages.
Beier et al., Telomere Dynamics in Patients with del (5q) MDS Before and Under Treatment With Lenalidomide, Lukemia Research, 39 (2015) 1292-1298.
Jay R. Thiagarajah et al. "Discovery and Development of Antisecretory Drugs for Treating Diarrheal Diseases", Clinical Gastroenterology and Hepatology, vol. 12, No. 2, Feb. 1, 2014, pp. 204-209 (from 0014JP1).
Yde, et al. "Characterization of AQPs in Mouse, Rat, and Human Colon and Their Selective Regulation by Bile Acids", Frontiers in Nutrition, vol. 3, Article 46, 2016.
Jeppesen "Spectrum of Short bowel Syndrome in Adults" Journal of Parenteral Enteral Nutrition, 2014, 38(1 Suppl), 38S-44S.
Juckett "Evaulation of Chronic Diarrhea", Am Fam Physician,84(10): 1119-1126, 2011.
Sagar, N.M., Duboc, H., Kay, G.L. et al. The pathophysiology of bile acid diarrhoea: differences in the colonic microbiome, metabolome and bile acids. Sci Rep 10,20436 (2020). https://doi.org/10.1038/s41598-020-77374-7.
Kumpf, "Pharmacologic Management of Diarrhea in Patients With Short Bowel Syndrome", Journal of Parenteral and Enteral Nutrition, vol. 38 Supplement 1, May 2014 38S-44S.

(Continued)

*Primary Examiner* — Kevin E Weddington
(74) *Attorney, Agent, or Firm* — Ballard Spahr LLP

(57) ABSTRACT

Presented herein are methods for treating bile acid diarrhea, short bowel syndrome (SBS), and cholecystectomy-associated diarrhea by administering to a patient in need thereof, an inhibitor of chloride-ion transport in an amount sufficient to treat diarrhea. In particular embodiments, infants, and juveniles with SBS are treated with an inhibitor of chloride-ion transport in an amount sufficient to treat diarrhea. Treatment of diarrhea includes the treatment of the diarrhea as well as the pain, abdominal discomfort and other symptoms associated with diarrhea. In one embodiment, the inhibitor of chloride-ion transport is crofelemer.

13 Claims, No Drawings

(56) References Cited

OTHER PUBLICATIONS

Schalamon J, Mayr JM, Hollwarth ME. Mortality and economics in short bowel syndrome. Best Pract Res Clin Gastroenterol. 2003;17(6):931-942.
Thompson JS. Short Bowel Syndrome and Malabsorption—Causes and Prevention. Viszeralmedizin. 2014;30(3):174-178.
Tappenden KA. Pathophysiology of short bowel syndrome: considerations of resected and residual anatomy. JPEN J Parenter Enteral Nutr. 2014;38(1 Suppl):14S-22S.
Field M. Intestinal ion transport and the pathophysiology of diarrhea. J Clin Invest. 2003;111(7):931-943.
Thiagarajah JR, Donowitz M, Verkman AS. Secretory diarrhoea: mechanisms and emerging therapies. Nat Rev Gastroenterol Hepatol. 2015,12(8):446-457.
Thiagarajah JR, Verkman AS. Chloride channel-targeted therapy for secretory diarrheas. Curr Opin Pharmacol. 2013;13(6):888-894.
Hasosah M, Lemberg DA, Skarsgard E, Schreiber R. Congenital short bowel syndrome: a case report and review of the literature. Can J Gastroenterol. 2008;22(1):71-74.
Weale AR, Edwards AG, Bailey M, Lear PA. Intestinal adaptation after massive intestinal resection. Postgrad Med J. 2005;81(953):178-184.
Stringer MD, Puntis JW. Short bowel syndrome. Arch Dis Child. 1995;73(2):170-173.
Guarino A, Lo Vecchio A, Berni Canani R. Chronic diarrhoea in children. Best Pract Res Clin Gastroenterol. 2012;26(5):649-661.
Guandalini S, Vaziri H. Diarrhea Diagnostic and Therapeutic Advances. 2010.
Clay PG, Crutchley RD. Noninfectious Diarrhea in HIV Seropositive Individuals: a Review of Prevalence Rates, Etiology, and Management in the Era of Combination Antiretroviral Therapy. Infectious Diseases and Therapy. 2014;3(2):103-122.
Hussar DA, Lye A. Vortioxetine hydrobromide, crofelemer, and teduglutide. Journal of the American Pharmacists Association. 54(1):91-94.
D'Antiga, Lorenzo; Goulet, Olivier Intestinal Failure in Children: The European View Journal of Pediatric Gastroenterology and Nutrition: Feb. 2013—vol. 56—Issue 2—p. 118-126.
MacArthur RD, Hawkins TN, Brown SJ, et al. Efficacy and safety of crofelemer for noninfectious diarrhea in HIV-seropositive individuals (ADVENT trial): A randomized double-blind, placebo-controlled, two-stage study. HIV Clin Trials 2013; 14:261-273.
Holodniy, M, Koch J, Mistal M, et al. A randomized double-blind, placebo-controlled phase II study to assess the safety and efficacy of orally administered SP-303 for the symptomatic treatment of diarrhea in patients with AIDS. Am J Gastroenterol 1999; 94: 3267-3273.
Mangel A and Chaturvedi P. Evaluation of crofelemer in the treatment of diarrhea-predominant irritable bowel syndrome patients. Digestion 2008; 78: 180-186.
Nee J, Salley, K, Ludwig AG, et al. Randomized clinical trial: Crofelemer treatment in women with diarrhea-predominant irritable bowel syndrome. Clin Transl Gastroenterol 2019: 10: e00110. https://doi.org/10.14309/ctg.
DiCesare D, DuPont HL, Mathewson JJ, et al. A double-blind placebo-controlled study of SP-303 (Provir) in the symptomatic treatment of acute diarrhea among travelers to Jamaica and Mexico. Am J Gastroenterol 2002; 97: 2585-2588.
Tradtrandip, L, Namkung W and Verkman AS. Crofelemer, an antisecretory antidiarrheal proanthocyanadin oligomer extracted from Croton lechleri, targets two distinct intestinal chloride channels. Mol Pharmacol 2010; 77: 69-78.
Gabriel SE, Davenport SE, Steagall RJ, et al. A novel plant-derived inhibitor of cAMP-mediate fluid and chloride secretion. Am J Physiol 276 (Gastrointest Liver Physiol 39) 1999; G58-G63.
Bardhan PK, Khan WA, Ahmed S, et al. Evaluation of safety and efficacy of a novel antisecretory antidiarrheal agent, crofelemer (NP-303), in combination with a single oral dose of azithromycin for the treatment of acute dehydrating diarrhea caused by Vibrio cholera. 43rd Conference on Cholera and Other Bacterial Enteric Diseases, Kyushu University, Fukuoka, Japan 2008.
Sharma A, Bolmall C, Dinakaran N, et al. Crofelemer improves acute infectious diarrhea symptoms. 48th Annual Interscience Conference on Antimicrobial Agents and Chemotherapy (ICAAC) and the Infectious Disease Society of America (IDSA) 46th Annual Meeting 2008; Abstract L-3595.
Lochs H, Dejong C, Hammarqvist F, Hebuterne X, Leon-Sanz M, Schütz T, van Gemert W, et al. ESPEN Guidelines on Enteral Nutrition: Gastroenterology. Clinical Nutrition. 2006;25:260-274.
Parrish CR, DiBaise JK. Managing the Adult Patient With Short Bowel Syndrome. Gastroenterology & Hepatology. 2017;13(10):600-608.
Sangild PT, Ney DM, Sigalet DL, Vegge A, Burrin D. Animal models of gastrointestinal and liver diseases. Animal models of infant short bowel syndrome: translational relevance and challenges. Am J Physiol Gastrointest Liver Physiol. Dec. 15, 2014;307(12):G1147-68.
Terrin G, Scipione A, De Curtis M. Update in pathogenesis and prospective in treatment of necrotizing enterocolitis. Biomed Res Int. 2014;2014:543765.
Camilleri, "Intestinal Secretory Mechanisms in Irritable Bowel Syndrome-Diarrhea", Clin Gastroenterol Hepatol. Jun. 2015 ; 13(6): 1051-1057. doi: 10.1016/j.cgh.2014.07.020.
Zella, et al. "Chronic Diarrhea in Children", Pediatrics in Review 2012;33;207.
Powers W (2022) Improved Electrolyte and Fluid Balance Results in Control of Diarrhea with Crofelemer in Patient with Short Bowel Syndrome: A Case Report. J Clin Gastroenterol Treat 8:086. doi. org/10.23937/2469-584X/1510086.
Vanderhoof JA, Langnas AN. Short-bowel syndrome in children and adults. Gastroenterology. 1997;113(5):1767-1778.
Wales PW, Christison-Lagay ER. Short bowel syndrome: epidemiology and etiology. Semin Pediatr Surg. 2010;19(1):3-9.
Short Bowel Syndrome. 2015. https://www.niddk.nih.gov/health-information/digestive-diseases/short-bowel-syndrome. Accessed Jul. 14, 2022.
Cagir B. Short Bowel Syndrome Clinical Presentation, emedicine Medscape 2015.
Joly F, Mayeur C, Messing B et al. Morphologic adaptation with preserved proliferation/transporter content in the colon of patients with short bowel syndrome. Am J Physiol Gastrointest Liver Physiol 2009: 297: G116-G123.
Long Vu, Chapter in Adult Short Bowel Syndrome, 2019.
Massironi S, Cavalcoli F, Rausa E, Invernizzi P, Braga M, Vecchi M. Understanding short bowel syndrome: Current status and future perspectives. Dig Liver Dis. Mar. 2020;52(3):253-261.
Thiagarajah, JR, Kamin, D, Aera S, et. al, Advances in Evaluation of Chronic Diarrhea in Infants. Gastroenterology vol. 154, Issue 8, Jun. 2018, pp. 2045-2059.
Camilleri M, Bile Acid diarrhea: prevalence, pathogenesis, and therapy, Gut Liver, 2015, vol. 9 No. 3, 332-339.
Yde, et al. Characterization of AQPs in Mouse, Rat, and Human Colon and Their Selective Regulation by Bile Acids, Front. Nutr. 3:46, Oct. 2016.
Third Party Observation for EP Application No. 20180808912 filed May 7, 2022.
Hornby, Drug discovery approaches to irritable bowel syndrome, Expert Opin. Drug Discov. 10(8), 2015.
Vitek, Bile Acid Malabsorption in Inflammatory Bowel Disease, Inflamm Bowel Dis, vol. 21, No. 2, Feb. 2015.
Notice of Observation Against a Patent Application for JP Application No. 2019-0566126 dated Feb. 9, 2022.
Acknowledgment of Protest and Notice of Observation for CA Application No. 3065800 dated Feb. 2, 2022.
Barkun, Bile acid malabsorption in chronic diarrhea: Pathophysiology and treatment, Can J Gastroenterol vol. 27, No. 11, Nov. 2013.
Camilleri, et al., The Role of Bile Acids in Chronic Diarrhea, Am J Gastroenterol. Oct. 2020; 115(10): 1596-1603.
Wedlake, et al., Systematic review: the prevalence of idiopathic bile acid malabsorption as diagnosed by SeHCAT scanning in patients

(56) References Cited

OTHER PUBLICATIONS with diarrhoea-predominant irritable bowel syndrome, Aliment Pharmacol Ther 30, 707-717, Jun. 2009.

* cited by examiner

METHODS AND COMPOSITIONS FOR TREATING BILE ACID DIARRHEA, DIARRHEA ASSOCIATED WITH SMALL INTESTINE RESECTION OR GALLBLADDER REMOVAL, AND SHORT BOWEL SYNDROME

FIELD OF THE INVENTION

The present invention is directed to methods of preventing, ameliorating and/or treating bile acid diarrhea or secretory diarrhea associated with short bowel syndrome (SBS) or gallbladder removal using a proanthocyanidin polymer composition from *C. lechleri*, such as crofelemer.

BACKGROUND

Bile Acid Diarrhea

Bile acids are synthesized in the liver from cholesterol and in conjugated form are transported into bile ducts. They then accumulate and are stored in the gallbladder where they flow into the duodenum following meal-stimulated gallbladder contraction. After delivery into the intestinal lumen, the vast majority are reabsorbed by the distal ileum into the portal circulation and returned to the liver. Uptake of bile acids by specific transport systems of hepatocytes takes place, and they are again secreted into bile. This process of recycling is called the enterohepatic circulation. The majority of bile acids are reabsorbed by the ileum in this recycling process. Usually less than 10% of the intestinal bile acids escapes reabsorption and is eliminated in the feces. (Pattni et al., *British Medical Bulletin*, Volume 92, Issue 1, 1 Dec. 2009, Pages 79-93).

When larger amounts of bile acids enter the large intestine, they stimulate water secretion and intestinal motility in the colon, which causes symptoms of chronic diarrhea, known as bile acid diarrhea or bile acid malabsorption. Bile acid diarrhea can be secondary to a gastrointestinal disorder or can be a primary disorder associated with excessive bile acid production or bile malabsorption. Based on the current understanding of the condition, bile acid diarrhea is categorized into three types. Type 1 pertains to bile acid malabsorption that is secondary to ileal resection or ileal inflammation (e.g. in Crohn's disease). Type 2 is the primary form and pertains to idiopathic bile acid malabsorption or overproduction. Type 3 is a form secondary to various gastrointestinal diseases including cholecystectomy (gallbladder removal), vagotomy, small intestinal bacterial overgrowth, radiation enteropathy, celiac disease, chronic pancreatitis, and cystic fibrosis (Pattni at Table 2).

The ileum is very efficient at absorbing the glyco- and taurine-conjugated forms of the bile salts because specialized bile acid transporters are highly expressed in the ileum. (Dawson et al., *J. Lipid Research,* 2009; 50 (12): 2340-57). When expression of these specialized transporters is reduced, the intestine is less efficient at bile acid reabsorption (Type 1 bile acid malabsorption). If intestinal motility is affected by gastro-intestinal surgery, or bile acids are deconjugated by small intestinal bacterial overgrowth, absorption is less efficient (Type 3 bile acid malabsorption). A very small proportion of patients have no obvious underlying disease/condition (Type 2 bile acid malabsorption) and may have mutations in a bile acid transporter gene. (Oelkers et al., *J. of Clinical Investigation,* 199; 99 (8): 1880-7).

Bile acid sequestrants are the main agents used to treat bile acid malabsorption. Cholestyramine, aluminum hydroxide, and colestipol, both in powder form, have been used for many years. Unfortunately many patients find them difficult to tolerate; although the diarrhea may improve, other symptoms such as pain and bloating may worsen.

Short Bowel Syndrome

Short bowel syndrome (SBS) is a complex condition characterized by malabsorption of fluids and nutrients due to congenital deficiencies, premature birth or surgical resection of small bowel segments. Consequently, patients suffer from symptoms such as diarrhea, malnutrition, dehydration and imbalances of fluids and salts. Specific symptoms and severity of the disease varies from one person to another depending on the age of the patient, the particular segment of small intestine resected, and extent of the resection. In infants, small intestine resection is performed to treat indications such as necrotizing enterocolitis, intestinal anomalies, and midgut volvulus. In older children and adults, Crohn's disease, vascular disease, malignancy, radiation enteritis, trauma, and adhesive obstruction are causative indications associated with resection (Vanderhoof et al., *Gastroenterology.* 1997; 113(5):1767-1778). Intestinal loss and compromised bowel adaptation leads to inadequate water and nutrient absorption (Schalamon et al., *Best Pract Res Clin Gastroenterol* 2003; 17(6):931-942). Most patients with SBS experience debilitating diarrhea that severely hinders their health outcomes and quality of life. (Kumpf, *JPEN J Parenter Enteral Nutr.* 2014; 38(1 Suppl):38S-44S). SBS-associated diarrhea may have several etiologies, therefore management of diarrhea in these patients is challenging and improved therapies are needed. No specific antidiarrheal drug has been studied and approved for SBS associated diarrhea.

SBS refers to the malabsorptive state caused by the physical or functional loss of significant portions of the small intestine. The main causes of SBS in children include congenital or perinatal diseases, such as intestinal atresia (narrowing or absence of a portion of the intestine), abdominal wall defects, malrotation (rotation of the gut outside the abdomen), volvulus (obstruction caused by twisting of the intestine), and long segment Hirschsprung's disease (damaged nerve cells in the colon leading to fecal buildup) (Wales, *Semin Pediatr Surg.* 2010; 19(1):3-9). However, the most common cause is necrotizing enterocolitis (NEC) accounting for 40-50% of infant SBS cases. (Thompson, *Viszeralmedizin.* 2014; 30(3):174-178). NEC is a devastating disease that largely affects premature infants where the intestine is invaded by bacteria causing an inflammatory response that ultimately destroys the wall of the intestine. (Terrin et al., *Biomed Res Int.* 2014; 2014:543765).

SBS is usually defined anatomically as less than 30% of normal intestinal length, which is less than 75 cm in children and less than 200 cm in adults. (Schalamon et al., *Best Pract Res Clin Gastroenterol.* 2003; 17(6):931-942). The reduction of intestinal length results in a reduced surface area for absorption of nutrients and a more rapid transit of intestinal contents. Poor nutrient processing capability leads to malabsorption-induced diarrhea, dehydration, electrolyte disturbances, and malnutrition. The symptoms and severity of SBS vary markedly and are dependent on the anatomic sections of the intestine that are resected, the length and absorptive capacity of the remaining bowel, and the presence of the active primary disease. (Tappenden, *JPEN J Parenter Enteral Nutr.* 2014; 38(1 Suppl):14S-22S).

Secretory diarrhea can be caused by a number of SBS-related stimuli such as bacterial infection, dihydroxy bile acids, hydroxylated fatty acids, or inflammatory mediators. SBS patients may suffer from bacterial overgrowth due to the resection of the terminal ileum and/or ileocecal valve which allows the migration of anaerobic bacteria into the small intestine. Furthermore, antimotility agents and acid-suppressing therapies cause bacterial overgrowth by disrupting normal bacterial flora. (Kumpf, *JPEN J Parenter Enteral Nutr.* 2014; 38(1 Suppl):38 S-44S). Bacterial overgrowth leads to the release of bacterial toxins that increase the levels of intracellular cyclic nucleotides that activate the apical CFTR Cl⁻ channels, hence the cause Cl⁻ secretion and increase intestinal permeability. (Thiagarajah et al., *Nat Rev Gastroenterol Hepatol.* 2015; 12(8):446-457). Bile acids are normally reabsorbed in the distal ileum with very little reaching the colon; however, SBS patients with ileal resections and colon-in-continuity may have spillover of bile salts into the colon. Deconjugation of these bile salts by colonic bacteria stimulate the movement of water and Cl⁻ into the colon. Similarly, fatty acids that reach the colon are hydroxylated by colonic bacteria, thereby making them amphophilic and induce secretion. Inflammatory mediators such as prostaglandins stimulate colonic secretion and cytokines may down-regulate fluid-absorptive mechanisms. (Field, *J Clin Invest.* 2003; 111(7): 931-943).

SBS patients are at increased risk for infection and experience impaired wound healing due to malnutrition. (Jeppesen, *JPEN J Parenter Enteral Nutr.* 2014; 38(1 Suppl):8S-13S). SBS can lead to hypotension and early kidney failure. A number of other chronic complications associated with SBS include hepatic and biliary disease, metabolic bone disease, small bowel bacterial overgrowth, enteric hyperoxaluria, and D-lactic acidosis. (Tappenden et al., *JPEN J Parenter Enteral Nutr.* 2014; 38(1 Suppl):14S-22S). Therefore, SBS-associated diarrhea and its related complications may be serious and life-threatening.

Based on the diverse etiologies of diarrhea, SBS patients are treated with a variety of antidiarrheal drugs including antimotility drugs, antisecretory agents, antibiotics and probiotics, bile acid-binding resins, and pancreatic enzymes. Management of diarrhea in these patients is challenging, and antidiarrheal treatment regimens must be individualized. In many cases, therapies may only be partially effective, have severe side effects, have potential for addiction, and have contraindications. Regimen optimization and careful consideration of potential drug-drug interactions are necessary (Kumpf, *JPEN J Parenter Enteral Nutr.* 2014; 38(1 Suppl): 38S-44S). The development of a drug for the treatment of SBS with a low potential for drug-drug interactions, effects on drug metabolism, or abuse potential would provide an important benefit for subjects and substantially improve the overall health and quality of life for patients with SBS.

Therefore, diarrhea associated with bile acid diarrhea, small bowel resection, cholecystectomy, and SBS represents an important and unmet clinical need requiring more effective management.

SUMMARY

Disclosed herein are methods of and compositions for preventing, ameliorating and/or treating diarrhea in subjects suffering from bile acid diarrhea, short bowel syndrome (SBS), diarrhea associated with small bowel resection, or post-cholecystectomy diarrhea using proanthocyanidin polymer compositions from *C. lechleri*, particularly crofelemer.

In one aspect, provided herein are methods of treating bile acid diarrhea in a subject, comprising administering to a subject in need thereof a composition comprising an effective amount of a proanthocyanidin polymer composition from *C. lechleri*, preferably crofelemer, to treat, or ameliorate diarrhea in the subject. In other embodiments, methods of treatment of bile acid diarrhea are provided by administration of a proanthocyanidin polymer composition, particularly crofelemer, to a subject, preferably a human, suffering from bile acid diarrhea, in which the administration results in an improvement in nutritional status, hydration and/or electrolyte balance of the subject. In other embodiments, treating bile acid diarrhea in a subject, comprising administering to a subject in need thereof a composition comprising an effective amount of a proanthocyanidin polymer composition from *C. lechleri*, preferably crofelemer, to treat, or ameliorate diarrhea in the subject. In other embodiments, compositions for treating bile acid diarrhea in a subject in need thereof are provided and comprise a proanthocyanidin polymer composition, particularly crofelemer.

In certain embodiments, the subject has Type 1, Type 2, or Type 3 bile acid diarrhea. In certain embodiments, the subject has SBS. In certain embodiments, the subject has small intestinal bacterial overgrowth, radiation enteropathy, celiac disease, or chronic pancreatitis. In certain embodiments, the subject had a vagotomy, cholecystectomy, ileal resection, duodenal resection, or a jejunal resection. In certain embodiments, the subject does not have inflammatory bowel disease, inflammatory bowel syndrome, or Crohn's disease.

In certain embodiments, the subject has above normal amounts of bile acid in their stool, below normal levels of bile acid absorption as indicated by measuring radio-labeled selenium homocholic acid taurine in the body a few days after ingestion, or above normal levels of 7-alpha-hydroxy-4-cholesten-3-one (C4) in their blood.

In another aspect, provided herein are methods of treating SBS in a subject, comprising administering to a subject in need thereof a composition comprising an effective amount of a proanthocyanidin polymer composition from *C. lechleri*, preferably crofelemer, to treat, or ameliorate SBS in infants, juveniles, adolescents, or adults. In embodiments, methods of treatment of SBS are provided by administration of a proanthocyanidin polymer composition, particularly crofelemer, to a subject, preferably a human, suffering from SBS, in which the administration results in an improvement in nutritional status, hydration and/or electrolyte balance of the subject. In other embodiments, compositions for treating SBS in a subject in need thereof are provided and comprise a proanthocyanidin polymer composition, particularly crofelemer.

The SBS may be due to surgical resection or congenital abnormalities. In one embodiment, the subject to be treated is an infant, and small intestine resection was a result of treatment for necrotizing enterocolitis, intestinal anomalies, or midgut volvulus. In specific embodiments, the SBS was caused by intestinal atresia, abdominal wall defect, malrotation, volvulus, long segment Hirschsprung's disease. In another specific embodiment, the SBS was caused by necrotizing enterocolitis. In certain embodiments, the subject to be treated is an infant within 1 week of birth, within 2 weeks of birth, within 1 month of birth, or within 6 months of birth. In certain embodiments, the infant is premature or was born prematurely.

In one embodiment, the subject to be treated is a non-infant juvenile, adolescent or an adult and small intestine resection was a result of treatment for Crohn's disease, vascular disease, malignancy, radiation enteritis, trauma, or adhesive obstruction.

In specific embodiments, the subject to be treated has less than 30% of the normal small bowel length, less than 25% of the normal small bowel length, less than 20% of the normal small bowel length, or less than 15% of the normal small bowel length and, in certain embodiments, has at least 2%, at least 3%, at least 5% or at least 10% of the normal small bowel length remaining.

In specific embodiments, provided are methods of treatment, prevention or amelioration of symptoms of SBS in which the subject exhibits dehydration, malnutrition and/or electrolyte imbalance. In specific embodiments, the subject is administered parenteral nutrition. In other embodiments, the subject exhibits a hepatic or biliary disorder, for example cholestasis in which direct bilirubin is greater than 2 mg/dL.

In other aspects, provided herein are methods of treating diarrhea in a subject who had a small intestine resection, comprising administering to a subject in need thereof a composition comprising an effective amount of a proanthocyanidin polymer composition from *C. lechleri*, preferably crofelemer, to treat, or ameliorate diarrhea in the subject. In other embodiments, methods of treatment of diarrhea in a subject who had a small intestine resection are provided by administration of a proanthocyanidin polymer composition, particularly crofelemer, to the subject, preferably a human, suffering from diarrhea, in which the administration results in an improvement in nutritional status, hydration and/or electrolyte balance of the subject. In certain embodiments, the subject had an ileal resection, duodenal resection, or a jejunal resection. In certain embodiments, the subject does not have Crohn's disease. In other embodiments, compositions for treating diarrhea associated with a small intestine resection in a subject in need thereof are provided and comprise a proanthocyanidin polymer composition, particularly crofelemer.

In specific embodiments, the subject to be treated has less than 70% of the normal small bowel length, less than 60% of the normal small bowel length, less than 50% of the normal small bowel length, less than 40% of the normal small bowel length, less than 30% of the normal small bowel length, or less than 20% of the normal small bowel length.

In yet another aspect, provided herein are methods of treating cholecystectomy-associated diarrhea in a subject, comprising administering to a subject in need thereof a composition comprising an effective amount of a proanthocyanidin polymer composition from *C. lechleri*, preferably crofelemer, to treat, or ameliorate diarrhea in the subject. In other embodiments, methods of treatment of cholecystectomy-associated diarrhea are provided by administration of a proanthocyanidin polymer composition, particularly crofelemer, to a subject, preferably a human, suffering from cholecystectomy-associated diarrhea, in which the administration results in an improvement in nutritional status, hydration and/or electrolyte balance of the subject. In other embodiments, compositions for treating cholecystectomy-associated diarrhea in a subject in need thereof are provided and comprise a proanthocyanidin polymer composition, particularly crofelemer.

In certain embodiments, the crofelemer is an enterically protected formulation.

In certain embodiments, the subject exhibits Grade 1, Grade 2, Grade 3 or Grade 4 diarrhea in accordance with the Common Toxicity Criteria from the National Cancer Institute or based on the various diarrheal grades defined by the National Institutes of Health.

In various embodiments, the administration comprises: administering about 100 mg to about 1000 mg per day; administering about 125 mg per day; administering about 250 mg per day; administering about 500 mg per day; administering about 1000 mg per day; administering about 125 mg two times per day; administering about 250 mg two times per day; or administering about 500 mg two times per day of crofelemer, particularly, enterically protected crofelemer formulated as a tablet for oral administration, to a subject in need thereof. In other embodiments, the crofelemer is formulated for oral administration but is not enterically protected, e.g., does not have an enteric coating. In other embodiments, the dosage of the proanthocyanidin polymer composition is bioequivalent to about 250 mg to about 1000 mg per day; about 250 mg per day; about 500 mg per day; about 1000 mg per day; about 125 mg two times per day; about 250 mg two times per day; or about 500 mg two times per day of an oral dosage form of crofelemer that enterically protected.

In certain embodiments, particularly for pediatric use, the administration comprises administering from 1 to 10 mg/kg, specifically about 1 mg/kg, 2 mg/kg, 5 mg/kg, 7 mg/kg or 10 mg/kg crofelemer once daily or, more preferably, twice daily, or even three times daily. The crofelemer may be formulated in a solid oral dosage form but is more preferably formulated in liquid form for ease of administration to the infant or juvenile. For example, the crofelemer may be dissolved at concentrations of 20 µg/ml to 2 mg/ml crofelemer. The crofelemer may be an enteric coated powder or granules or dissolved in an aqueous formulation without an enteric coating. In certain embodiments, the crofelemer formulation is administered through a feeding tube. Alternatively, the formulation is delivered orally. In a specific embodiment, the crofelemer is dissolved, and is not enteric coated, at a concentration of 20 µg/ml to 2 mg/ml and is administered at a dose of 1 mg/kg to 10 mg/kg twice a day either orally or through a feeding tube.

The dosages may be the amount of a composition containing a proanthocyanidin polymer composition from *C. lechleri*, for example, SB300, that is bioequivalent to the dose of an enteric protected formulation of crofelemer.

In one embodiment, a subject is considered treated if the subject demonstrates one or more of a decrease in the number of bowel movements per day, a decrease in the number of watery bowel movements per day, an improvement in the daily or weekly abdominal score for pain or discomfort, an improvement in the score for daily stool consistency, a decrease in stool consistency score (from watery to formed), a decrease in the number of days per week that subjects experienced urgency, a decrease in the number of days per week that the subject experienced fecal incontinence.

Other embodiments are disclosed infra.

DETAILED DESCRIPTION

Bile Acid Diarrhea

Bile acid diarrhea is associated with reduced absorption of bile acid. When larger amounts of bile acids enter the large intestine, the bile acids stimulate water secretion and intestinal motility in the colon, which causes symptoms of diarrhea. Bile acid is absorbed in the small intestines and when the absorption is reduced or when bile acid production is too high, the bile acid will enter the large intestines at greater concentrations than it would otherwise. Bile acids may be absorbed in the colon and may stimulate water and chloride ion secretion into the colon, which may cause secretory diarrhea. A number of conditions or diseases may lead to an abnormal amount of bile acid entering the large intestines. Such conditions include ileal resection, ileal inflammation (e.g. in Crohn's disease), idiopathic bile acid malabsorption or overproduction, cholecystectomy (gallbladder removal), vagotomy, small intestinal bacterial overgrowth, radiation enteropathy, celiac disease, and chronic pancreatitis. Bile acid sequestrants are the main agents used to treat bile acid malabsorption or overproduction. Provided herein are methods of addressing the secretory diarrhea associated with malabsorption or overproduction that improve the nutritional status, hydration, electrolyte balance, health, quality of life and prognosis for such patients.

Short Bowel Syndrome

SBS results in a reduced surface area for absorption of nutrients and a more rapid transit of intestinal contents. Many SBS patients require long term parenteral nutrition and may experience serious metabolic complications, including hepatic and biliary disorders, increased risk of infection and other serious, chronic complications. Secretory diarrhea may be caused by a number of SBS-related stimuli, such as bacterial infection, dihydroxy bile acids, hydroxylated fatty acids, or inflammatory mediators. Antimotility and acid-suppressing therapies can cause bacterial overgrowth, promoting secretory diarrhea. (Kumpf, *JPEN J Parenter Enteral Nutr.* 2014; 38(1 Suppl.):38S-44S). SBS patients are treated with a variety of anti-diarrhea drugs, including anti-motility drugs, anti-secretory agents, and antibiotics. In all aspects, SBSs are life-threatening conditions with high chance of mortality or life-long morbidity. Provided herein are methods of addressing the secretory diarrhea associated with SBS that improve the nutritional status, hydration, electrolyte balance, health, quality of life and prognosis for SBS patients.

In one embodiment, the subject to be treated is a non-infant juvenile (between 1 and 12 years old), adolescent (i.e., pubescent or just post-pubescent, e.g., between about 13 and about 18 years old) or an adult, and has bile acid diarrhea.

In one embodiment, the subject to be treated is an infant (less than one year of age), and had a small intestine resection as a result of treatment for necrotizing enterocolitis, intestinal anomalies, or midgut volvulus.

In one embodiment, the subject to be treated is a non-infant juvenile (between 1 and 12 years old), adolescent (i.e., pubescent or just post-pubescent, e.g., between about 13 and about 18 years old) or an adult, and had a small intestine resection as a result of treatment for Crohn's disease, vascular disease, malignancy, radiation enteritis, trauma, or adhesive obstruction.

In one embodiment, the subject to be treated is a non-infant juvenile (between 1 and 12 years old), adolescent (i.e., pubescent or just post-pubescent, e.g., between about 13 and about 18 years old) or an adult, and has been diagnosed with SBS.

In one embodiment, the subject to be treated is a non-infant juvenile (between 1 and 12 years old), adolescent (i.e., pubescent or just post-pubescent, e.g., between about 13 and about 18 years old) or an adult, and had a cholecystectomy.

Proanthocyanidin polymer compositions of *C. lechleri*, such as crofelemer, and more particularly, enteric coated crofelemer formulated for oral administration, but also SB300, reduce, ameliorate, prevent or eliminate the SBS symptoms or bile acid diarrhea in a subject.

The methods disclosed herein involved the administration of effective amounts of a proanthocyanidin polymer, e.g., crofelemer, to subjects having secretory diarrhea associated with SBS or bile acid malabsorption or overproduction.

I. DEFINITIONS

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a compound" includes a plurality of compounds. Thus, for example, a reference to "a method" includes one or more methods, and/or steps of the type described herein and/or which will become apparent to those persons skilled in the art upon reading this disclosure.

"Ameliorate," "amelioration," "improvement" or the like refers to, for example, a detectable improvement or a detectable change consistent with improvement that occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range between about any two of these values. Such improvement or change may be observed in treated subjects as compared to subjects not treated with crofelemer, where the untreated subjects have, or are subject to developing, the same or similar disease, condition, symptom or the like. Amelioration of a disease, condition, symptom or assay parameter may be determined subjectively or objectively, e.g., self-assessment by a subject(s), by a clinician's assessment or by conducting an appropriate assay or measurement. Amelioration may be transient, prolonged or permanent or it may be variable at relevant times during or after crofelemer is administered to a subject or is used in an assay or other method described herein or a cited reference, e.g., within timeframes described infra, or about 1 hour after the administration or use of crofelemer to about 7 days, 2 weeks, 28 days, or 1, 3, 6, 9 months or more after a subject(s) has received such treatment.

The "modulation" of, e.g., a symptom, level or biological activity of a molecule, or the like, refers, for example, that the symptom or activity, or the like is detectably increased or decreased. Such increase or decrease may be observed in treated subjects as compared to subjects not treated with crofelemer, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively. Modulation may be transient, prolonged or permanent or it may be variable at relevant times during or after crofelemer is administered to a subject or is used in an assay or other method described herein or a cited reference, e.g., within times descried infra, or about 1 hour of the administration or use of crofelemer to about 2 weeks, 28 days, 3, 6, 9 months or more after a subject(s) has received crofelemer.

As used herein, "subject" includes an animal, including a person, such as adult or pediatric persons.

The language "a therapeutically effective amount" of a compound refers to an amount of crofelemer which is effective, upon single or multiple dose administration to the subject.

The language "a prophylactically effective amount" of a compound refers to an amount of crofelemer which is effective, upon single or multiple dose administration to the subject, in preventing or delaying onset of symptoms.

The term "administration" or "administering" includes routes of introducing crofelemer to a subject to perform its intended function. Examples of routes of administration that may be used include oral, injection, inhalation, vaginal, rectal, topical, and transdermal. The pharmaceutical preparations may be given by forms suitable for each administration route. For example, these preparations are administered in tablet or capsule form, by injection, inhalation, ointment, or suppository. Administration may also be by injection, infusion or inhalation; topical by lotion or ointment; and rectal by suppositories. Oral administration is preferred. Depending on the route of administration, crofelemer can be coated with or disposed in a selected material to protect it from natural conditions that may detrimentally affect its ability to perform its intended function. Crofelemer can be administered alone, or in conjunction with either another agent or agents as described above or with a pharmaceutically-acceptable carrier, or both. Exemplary enteric coated forms of crofelemer are described in, for example, U.S. Pat. No. 7,556,831.

Administration "in combination with" one or more further therapeutic agents includes simultaneous (concurrent) and consecutive administration in any order.

The phrase "pharmaceutically acceptable" refers to crofelemer as described herein, compositions containing crofelemer, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body.

The term "treat" or "treatment" as used herein is intended to include the reduction or amelioration of the progression, severity, and/or duration of a condition or one or more symptoms of the condition, e.g., bile acid diarrhea or SBS.

For example, treating bile acid diarrhea or SBS may include an improvement of the following symptoms of bile acid diarrhea or SBS, including, for example, a decrease in the number of bowel movements per day (daily frequency of stools), a decrease in the number of watery bowel movements per day (daily frequency of abnormal stools), a decrease in symptom frequency (urgency, fecal incontinence), a decrease in symptom severity (abdominal pain or discomfort), a decrease in daily stool consistency score (watery to formed), a decrease in stool consistency leading to formed stools from watery stools, improvement in nutritional status, hydration and/or electrolyte balance, improvement in hepatic or biliary disease, or reduction in morbidity or risk of death.

The term "obtaining" as in "obtaining crofelemer" is intended to include purchasing, synthesizing, isolating, extracting or otherwise acquiring crofelemer.

II. ACTIVE COMPOUNDS

A. Proanthocyanidins

Proanthocyanidins are a group of condensed tannins. Crude extracts from medicinal plants, for example, *Pycanthus angolenis* and *Baphia nitida*, have been shown to have antidiarrheal qualities in animal tests (Onwukaeme and Anuforo, 1993, Discovery and Innovation, 5:317; Onwukaeme and Lot, 1991, Phytotherapy Res., 5:254). Crude extracts which contain tannins, in particular extracts from carob pods and sweet chestnut wood, have been proposed as treatments or prophylactics (U.S. Pat. No. 5,043,160; European Patent No. 481,396).

Proanthocyanidins are comprised of at least two or more monomer units that may be of the same or different monomeric structure. The monomer units (generally termed "leucoanthocyanidin") are generally monomeric flavonoids which include catechins, epicatechins, gallocatechins, epigallocatechins, flavanols, flavonols, and flavan-3,4-diols, leucocyanidins and anthocyanidins. Therefore, the polymer chains are based on different structural units, which create a wide variation of polymeric proanthocyanidins and a large number of possible isomers (Hemingway et al., 1982, J. C. S. Perkin, 1:1217). Larger polymers of the flavonoid 3-ol units are predominant in most plants, and are found with average molecular weights above 2,000 daltons, containing 6 or more units (Newman et al., 1987, Mag. Res. Chem., 25:118).

Proanthocyanidin polymers are found in a wide variety of plants, particularly those with a woody habit of growth (e.g., *Croton* spp. and *Calophyllum* spp.). A number of different *Croton* tree species, including *Croton sakutaris*, *Croton gossypifolius*, *Croton palanostima*, *Croton lechleri*, *Croton erythrochilus* and *Croton draconoides*, found in South America, produce a red viscous latex sap called Sangre de Drago or "Dragon's Blood". U.S. Pat. No. 5,211,944 first described the isolation of an aqueous soluble proanthocyanidin polymer composition from *Croton* spp. and the use of the composition as an antiviral agent (See also Ubillas et al., 1994, Phytomedicine, 1:77). The proanthocyanidin polymer composition was shown to have antiviral activity against a variety of viruses including, respiratory syncytial, influenza, parainfluenza and herpes viruses. U.S. Pat. No. 5,211,944 also discloses the isolation of an aqueous soluble proanthocyanidin polymer composition from *Calophyllum inophyllum* and the use of this composition as an antiviral agent.

Exemplary proanthocyanidin polymer compositions useful in the methods presented herein are preferably isolated from a *Croton* spp. or *Calophyllum* spp. by any method known in the art. For example, the proanthocyanidin polymer composition may be isolated from a *Croton* spp. or *Calophyllum* spp. by the method disclosed in U.S. Pat. No. 5,211,944 or in Ubillas et al., 1994, Phytomedicine 1: 77-106.

In one specific embodiment, a proanthocyanidin polymer composition useful in the methods presented herein is crofelemer.

Crofelemer is an oligomeric proanthocyanidin extracted and purified from the red, viscous latex of the plant *Croton lechleri* of the family Euphorbiaceae. The plant is widely distributed throughout tropical Central America and South America and is widely recognized by ethnobotanists and local healers for its medicinal properties (McRae 1988), including for the treatment of diarrhea. Crofelemer is believed to exert its anti-diarrhea effect through luminal blockade and/or modulation of CFTR (cystic fibrosis transmembrane conductance regulator) chloride (Cl—) channel. Crofelemer has demonstrated in vitro activity against cholera toxin, forskolin, *E. coli* LT and STa toxin-mediated Cl-secretion, and to normalize electrolyte and fluid accumulation in CT-treated mice (Gabriel 1999, Fischer 2004, Adam 2005) via its effects on the CFTR chloride channel. Crofelemer also significantly improved the secretory diarrhea in humans due to enterotoxigenic *E. coli* (DiCesare 2002), which is also thought to evoke secretory diarrhea through activation of CFTR (Kunzelmann 2002). Blockade or inhibitory modulation of the CFTR channel could be anticipated to have negative consequences in man, even mimicking cystic fibrosis. However, crofelemer has virtually no systemic bioavailability in humans. When studied, the results indicated that there was little or no absorption of crofelemer from the GI tract, and that crofelemer was well tolerated by normal male subjects. Thus, the site of action of crofelemer is topical in the gastrointestinal tract.

Crofelemer (CAS 148465-45-6) is an oligomeric proanthocyanidin of varying chain lengths derived from the Dragon's Blood *Croton lecheri* of the family Euphorbiaceae. Crofelemer has an average molecular weight ranging between approximately 1500 daltons and approximately 2900 daltons. The monomers comprising crofelemer comprise catechin, epicatechin, gallocatechin, and epigallocatechin. The chain length of crofelemer ranges from about 3 to about 30 units with an average chain length of about 7-8 units. The structure of crofelemer is shown below.

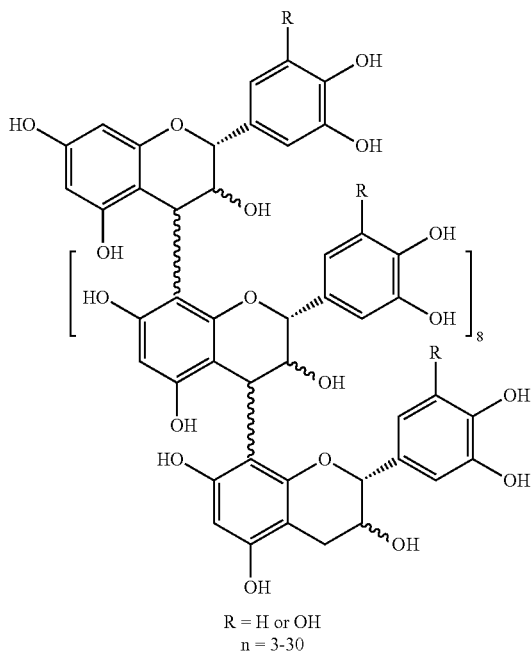

R = H or OH
n = 3-30

Wherein the average n=6.

Another method for isolating crofelemer can be found in U.S. Patent Publication No. 2005/0019389, the contents of which are expressly incorporated herein.

In addition, the proanthocyanidin polymer composition may be SB 300, as described, for example, by Fischer, H. et al., (2004, *J. Ethnopharmacol.*, 93(2-3):351-357). SB300 is a natural product extract that is particularly amenable for use in a non-enterically coated or protected formulations and compositions. In an embodiment, a pharmaceutically acceptable composition comprising a proanthocyanidin polymer from *Croton lechleri* and employed in the treatment methods of the invention can be obtained from *C. lechleri*, e.g., as described in WO 00/47062 to Shaman Pharmaceuticals, Inc., the contents of which are incorporated herein, and formulated as a food or dietary supplement or nutraceutical formulation, especially in a non-enterically coated formulation.

In other embodiments, raw latex obtained from a *Croton* species or a *Calophyllum* species or an extract obtained from a *Croton* species or a *Calophyllum* species are useful in the methods presented herein. Exemplary extracts are described in Persinos et al., 1979, *J. Pharma. Sci.* 68:124 and Sethi, 1977, *Canadian J. Pharm. Sci.* 12:7.

III. METHODS OF TREATMENT

Provided herein are methods of treating, preventing, or ameliorating the symptoms of bile acid diarrhea, comprising administering to a subject in need thereof an effective amount of a proanthocyanidin polymer composition of *C. lechleri*, preferably, crofelemer, particularly an enterically protected form of crofelemer to treat, prevent or ameliorate the symptoms of bile acid diarrhea. The subject is preferably a human.

In one aspect, provided herein are methods of treating bile acid diarrhea in a subject, comprising administering to a subject in need thereof a composition comprising an effective amount of a proanthocyanidin polymer composition from *C. lechleri*, preferably crofelemer, to treat, or ameliorate diarrhea in the subject. In other embodiments, methods of treatment of bile acid diarrhea are provided by administration of a proanthocyanidin polymer composition, particularly crofelemer, to a subject, preferably a human, suffering from bile acid diarrhea, in which the administration results in an improvement in nutritional status, hydration, and/or electrolyte balance of the subject.

In certain embodiments, the subject has Type 1, Type 2, or Type 3 bile acid diarrhea. In certain embodiments, the subject has SBS. In certain embodiments, the subject has small intestinal bacterial overgrowth, radiation enteropathy, celiac disease, cystic fibrosis, or chronic pancreatitis. In certain embodiments, the subject had a vagotomy, cholecystectomy, duodenal resection, ileal resection, or a jejunal resection. In certain embodiments, the subject does not have inflammatory bowel disease, inflammatory bowel syndrome, or Crohn's disease.

In certain embodiments, the subject has above normal amounts of bile acid in their stool, below normal levels of bile acid absorption as indicated by measuring radio-labeled selenium homocholic acid taurine in the body a few days after ingestion (known as the $^{75}$SeHCAT scan), or above normal levels of 7a-hydroxy-4-cholesten-3-one (C4) in their blood. For a $^{75}$SeHCAT scan, in some embodiments, a 7-day $^{75}$SeHCAT retention value greater than 15%, 20%, or 25% is considered to be normal, with values less than 15%, 20%, or 25% abnormal or excessive bile acid loss. For a C4 bloods test, in some embodiments, serum levels of C4 greater than 50 ng/mL, 55 ng/mL, 60 ng/mL, 65 ng/mL, 70 ng/mL, or 75 ng/mL.

In one embodiment, treating bile acid diarrhea diarrhea means improvement of, for example, a decrease in the number of bowel movements per day (frequency), a decrease in the number of watery bowel movements per day, a decrease in symptom frequency (urgency, fecal incontinence), a decrease in symptom severity (abdominal pain or discomfort), a decrease in daily stool consistency score (watery to formed), or a decrease in stool consistency leading to formed stools from watery stools.

Also, provided herein are methods of treating, preventing, or ameliorating the symptoms of SBS, particularly, secretory diarrhea and gastrointestinal symptoms caused by and associated with SBS, comprising administering to a subject in need thereof an effective amount of a proanthocyanidin polymer composition of *C. lechleri*, preferably, crofelemer, particularly an enterically protected form of crofelemer to treat, prevent or ameliorate the symptoms of SBS. The subject is preferably a human.

In one embodiment, the subject to be treated is an infant, and small intestine resection was a result of treatment for necrotizing enterocolitis, intestinal anomalies, or midgut volvulus. In specific embodiments, the SBS was caused by intestinal atresia, abdominal wall defect, malrotation, or long segment Hirschsprung's disease. In certain embodiments, the infant suffers from necrotizing enterocolitis and has bowel resection. In certain embodiments, the treatment begins at birth, within 1 week of birth, within 2 weeks of birth, within 1 month of birth, within 2 months of birth, within 6 months of birth or within 1 year of birth. In certain embodiments, the infant is premature or was born prematurely, at least 2 weeks, 4 weeks, 5, weeks, 6 weeks, 8 weeks, or 10 weeks prematurely.

In one embodiment, the subject to be treated is a non-infant juvenile, an adolescent, or an adult and had a small intestine resection as a result of treatment for Crohn's disease, vascular disease, malignancy, radiation enteritis, trauma, or adhesive obstruction.

In specific embodiments, the subject had a small bowel resection that leaves less than 30% of the small bowel or normal intestine length, less than 25% of the small bowel or normal intestine length, less than 20% of the small bowel or normal intestine length, or less than 15% of the small bowel or normal intestine length, and, in certain embodiments, has at least 2%, at least 3%, at least 5% or at least 10% of the normal intestine length remaining. In certain embodiments, a portion of the large intestine or colon is also resected. In certain embodiments, the resection removes all or a portion of the duodenum, the jejunum or the ileum, or a combination of all or a portion of the duodenum and the jejunum, a combination of all or a portion of the jejunum and the ileum, or a combination of all or a portion of the duodenum, all of the jejunum, and all or a portion of the ileum.

In specific embodiments, the subject is administered parenteral nutrition and crofelemer. In certain embodiments, the subject is administered parenteral nutrition immediately after surgical resection to meet the nutritional needs of the subject along with crofelemer to address secretory diarrhea associated with SBS. Parenteral nutrition may be administered for the first 7 to 10 days, or even longer, such as 15, 20 or 30 days, after surgical resection, including cases in which the subject receives all nutrition or a portion of the subject's nutritional needs through parenteral nutrition. As the intestine adapts, the need for parenteral nutrition may be reduced and the subject may, in certain circumstances, be weaned off the need for parenteral nutrition. In specific embodiments, the subject may be administered crofelemer during the post-operative period during which parenteral nutrition is administered. Crofelemer may be administered in conjunction with parenteral nutrition chronically or even after the parenteral nutrition is reduced or stopped altogether as the subject adapts to a shorter small intestine.

In specific embodiments, the subject needs long term or life time parenteral nutrition and is also administered crofelemer long term, chronically or for life. Long term parenteral nutrition can result in serious metabolic complications, including hepatic and biliary disorders, such as, steatosis, fibrosis, and cholestasis, which can progress to fulminant liver failure. Accordingly, methods are provided for treating secretory diarrhea in subjects suffering from SBS who have a hepatic and/or biliary disorder. In certain embodiments, the administration of crofelemer reduces the severity or impact of the hepatic or biliary disorder, including steatosis, fibrosis or cholestasis, and reduces the risk or incidence of liver failure.

In specific embodiments, provided are methods of treating or ameliorating secretory diarrhea associated with SBS by administration of crofelemer to a subject suffering therefrom, wherein the secretory diarrhea is caused by one or a combination of increased intestinal motility, gastric hypersecretion, intestinal bacterial overgrowth, or steatorrhea. The methods provided include administration of the crofelemer with one or more other pharmaceutical agents that may treat or ameliorate one or more symptoms of SBS. The agent in combination may be chosen depending upon the cause of the secretory diarrhea. For example, if the cause is increased intestinal motility, the subject may be administered crofelemer in combination with loperamide, diphenoxylate and/or atropine, codeine, or opium tincture; if the cause is gastric hypersecretion, the crofelemer may be administered with one or more proton pump inhibitors and/or an $H_2$ antagonist or an aa-adrenergic receptor agonist; if the cause is intestinal bacterial overgrowth, then crofelemer is administered with antibiotics like rifaximin and/or probiotics (and in this case, the treatment may, in certain embodiments, not include anti-motility or acid reducing agents in the combination); and, if the cause is steatorrhea, then crofelemer is administered in combination with pancreatic enzyme replacement and/or bile acid replacement therapies. In certain embodiments, provided are methods of treating or ameliorating the symptoms of the secretory diarrhea associated with SBS comprising administering to a subject in need thereof (i) parenteral nutrition, (ii) a therapeutically effective amount of crofelemer, and (iii) a therapeutically effective amount of one or more of loperamide, diphenoxylate, atropine, a proton pump inhibitor, an $H_2$ antagonist, an $\alpha_2$-adrenergic receptor agonist, an antibiotic (like rifaximin), a probiotic, pancreatic enzyme replacement therapy, a bile acid replacement therapy and/or octreotide.

In one embodiment, treating SBS includes an improvement of the following symptoms of secretory diarrhea associated with SBS, including, for example, a decrease in the number of bowel movements per day (frequency), a decrease in the number of watery bowel movements per day, a decrease in symptom frequency (urgency, fecal incontinence), a decrease in symptom severity (abdominal pain or discomfort), a decrease in daily stool consistency score (watery to formed), or a decrease in stool consistency leading to formed stools from watery stools.

In other embodiments, treating SBS, and secretory diarrhea associated with SBS, includes an improvement in nutritional status of the subject, hydration, and/or electrolyte balance, weight gain and improvement in growth and development, particularly of infants or children, and in neurocognitive, musculoskeletal and/or cardiovascular symptoms associated with malnutrition. In certain embodiments, treating SBS, and the associated secretory diarrhea, includes an improvement in hypotension and kidney failure associated with SBS, an improvement in liver disease and a reduction in the risk of liver failure associated with SBS. In certain embodiments, treating SBS, and the associated secretory diarrhea, includes improvement in chronic complications associated with SBS, including hepatic and biliary disease, metabolic bone disease, small bowel bacterial overgrowth, enteric hyperoxaluria and/or D-lactic acidosis. In certain embodiments, treating SBS, and the associated secretory diarrhea, includes reducing the risk of infection and improved wound healing.

Improvement in one or more symptoms associated with secretory diarrhea associated with SBS may be measured from a baseline. The baseline may be determined in the days to week prior to treatment with crofelemer.

In other aspects, provided herein are methods of treating diarrhea in a subject who had a small intestine resection, comprising administering to a subject in need thereof a composition comprising an effective amount of a proanthocyanidin polymer composition from *C. lechleri*, preferably crofelemer, to treat, or ameliorate diarrhea in the subject. In other embodiments, methods of treatment of diarrhea in a subject who had a small intestine resection are provided by administration of a proanthocyanidin polymer composition, particularly crofelemer, to the subject, preferably a human, suffering from diarrhea, in which the administration results in an improvement in nutritional status, hydration and/or electrolyte balance of the subject. In certain embodiments, the subject had an ileal resection, a jejunal resection, or a duodenal resection. In certain embodiments, the subject does not have Crohn's disease.

In specific embodiments, the subject to be treated has less than 70% of the normal small bowel length, less than 60% of the normal small bowel length, less than 50% of the normal small bowel length, less than 40% of the normal small bowel length, less than 30% of the normal small bowel length, or less than 20% of the normal small bowel length.

In one embodiment, treating secretory diarrhea associated with the small intestine resection means improvement of, for example, a decrease in the number of bowel movements per day (frequency), a decrease in the number of watery bowel movements per day, a decrease in symptom frequency (urgency, fecal incontinence), a decrease in symptom severity (abdominal pain or discomfort), a decrease in daily stool consistency score (watery to formed), or a decrease in stool consistency leading to formed stools from watery stools.

In yet another aspect, provided herein are methods of treating cholecystectomy-associated diarrhea in a subject, comprising administering to a subject in need thereof a composition comprising an effective amount of a proanthocyanidin polymer composition from *C. lechleri*, preferably crofelemer, to treat, or ameliorate diarrhea in the subject. In other embodiments, methods of treatment of cholecystectomy-associated diarrhea are provided by administration of a proanthocyanidin polymer composition, particularly crofelemer, to a subject, preferably a human, suffering from cholecystectomy-associated diarrhea, in which the administration results in an improvement in nutritional status, hydration and/or electrolyte balance of the subject.

In one embodiment, treating secretory diarrhea associated with a cholecystectomy means improvement of, for example, a decrease in the number of bowel movements per day (frequency), a decrease in the number of watery bowel movements per day, a decrease in symptom frequency (urgency, fecal incontinence), a decrease in symptom severity (abdominal pain or discomfort), a decrease in daily stool consistency score (watery to formed), or a decrease in stool consistency leading to formed stools from watery stools.

In specific embodiments, the crofelemer is an enterically coated oral dosage form. In other embodiments, the crofelemer is an oral dosage form that is not enterically protected. For pediatric treatments, the dosage is adjusted accordingly based on body weight of the subject.

In certain embodiments, the crofelemer is administered until symptoms of SBS or diarrhea are ameliorated and then crofelemer is discontinued.

As will be readily apparent to one skilled in the art, the useful in vivo dosage to be administered and the particular mode of administration may vary depending upon the age, weight and mammalian species treated, the particular compounds employed, and/or the specific use for which these compounds are employed. The determination of effective dosage levels that is the dosage levels necessary to achieve the desired result, can be accomplished by one skilled in the art using routine pharmacological methods and in consultation with the data presented herein.

Crofelemer may be administered, for example, once a day, twice a day, three times a day, or four times or more often as necessary per day. Crofelemer may be administered in doses, for example of from about between 25 mg BID to about 3000 mg TID, preferably crofelemer is administered from between about 125 mg to about 1000 mg per day. In another embodiment, crofelemer is administered between 125 mg BID to about 500 mg BID depending of symptoms. In another embodiment, crofelemer is administered as 125 mg once daily. In another embodiment, crofelemer is administered as 125 mg BID. In another embodiment, crofelemer is administered as 500 mg BID. Crofelemer may be administered orally, for example, in tablet form, powder form, liquid form or in capsules. In preferred embodiments, the crofelemer is formulated as an enteric coated oral dosage form. In other embodiments, the crofelemer is an oral dosage form that is not enteric coated.

In certain embodiments, particularly for pediatric use, crofelemer is administered at a dose from 1 to 10 mg/kg, specifically about 1 mg/kg, 2 mg/kg, 5 mg/kg, 7 mg/kg or 10 mg/kg once daily or, more preferably, twice daily, or even three times daily. The crofelemer may be formulated in a solid oral dosage form but is more preferably formulated in liquid form for ease of administration to the infant or juvenile. For example, the crofelemer may be dissolved at concentrations of 20 µg/ml to 2 mg/ml crofelemer and the appropriate volume administered for the desired dosage of about 1 to 10 mg/kg. The crofelemer may be an enteric coated powder or granules or dissolved in an aqueous formulation without an enteric coating. In certain embodiments, the crofelemer formulation is administered through a feeding tube. Alternatively, the formulation is delivered orally. In a specific embodiment, the crofelemer is dissolved, and is not enteric coated, at a concentration of 20 µg/ml to 2 mg/ml and is administered at a dose of 1 mg/kg to 10 mg/kg twice a day either orally or through a feeding tube.

In exemplary embodiments, the subject is orally administered 125, 250, 500, or 1000 mg/day of enteric protected crofelemer or is administered a dose of a proanthocyanidin polymer composition, including crofelemer, that is bioequivalent to an oral dosage form of enteric coated crofelemer administered at 125, 250, 500, or 1000 mg/day.

In specific embodiments, the subject is administered 125 mg once daily or 125, 250 or 500 mg p.o. b.i.d (orally twice per day) enteric coated crofelemer or a dosage of a proanthocyanidin polymer composition bioequivalent to 125 mg once daily or 125, 250 or 500 mg p.o. b.i.d enteric coated crofelemer.

In specific embodiments, the subject is administered a dose of 2 mg/kg to 10 mg/kg twice daily enteric coated crofelemer or a dosage of a proanthocyanidin polymer composition bioequivalent to 2 mg to 10 mg/kg twice daily enteric coated crofelemer formulated for oral administration.

Other appropriate dosages for methods may be determined by health care professionals or by the subject. The amount of crofelemer administered daily may be increased or decreased based on the weight, age, health, sex or medical condition of the subject. One of skill in the art would be able to determine the proper dose for a subject based on this disclosure and the data presented in the Examples, which follow.

In other embodiments, the subject is treated with crofelemer for 2, 4, 6, 8, 10, 12, 14, 16, 18, 20, 22, 24 or more weeks or 26 or more weeks or may be administered chronically or as long as the subject has secretory diarrhea or chronic secretory diarrhea.

In some embodiments, the subject is treated with crofelemer at a first daily dose for an initial treatment phase (e.g., a period of time until the diarrhea has been treated) and at a second lower daily dose for a maintenance phase. The first daily dose can be at least two times greater than the second daily dose. For example, in some embodiments, first daily dose is 250 mg of crofelemer and the second daily dose is 125 mg of crofelemer. In some embodiments, the first treatment phase is 2, 4, 6, 8, 10, or 12 weeks. In some embodiments, the maintenance phase is 2, 4, 6, 8, 10, 12, 14, 16, 18, 20, 22, 24, 26, or more weeks.

Cotherapies with crofelemer can include administration of bile acid sequestrants (e.g., cholestyramine, aluminum hydroxide, and colestipol), loperamide, diphenoxylate, atropine, proton pump inhibitor, an H2 antagonist, an a2-adrenergic receptor agonist, an antibiotic (like rifaximin or azithromycin), a probiotic, pancreatic enzyme replacement therapy and/or bile acid replacement therapy or octreotide Subjects in need thereof include subjects having or that are susceptible to or who have SBS, a small intestine resection, a cholecystectomy, or bile acid diarrhea.

IV. PHARMACEUTICAL PREPARATIONS

Also provided herein are pharmaceutical compositions, comprising an effective amount of a crofelemer described herein and a pharmaceutically acceptable carrier. In a further embodiment, the effective amount is effective to treat SBS, bile acid diarrhea, or diarrhea associated with a cholecystectomy or a small intestine resection.

Examples of the preparation and use of crofelemer have been described in U.S. Pat. No. 7,556,831, US Patent Publication 20070254050 and US Patent Publication 20080031984, all of which are incorporated herein by reference in their entirety.

One embodiment includes pharmaceutical compositions comprising crofelemer and a pharmaceutically acceptable carrier. In preferred embodiments, the pharmaceutical composition is an enterically protected oral dosage form, such as a tablet or capsule. Alternatively, the pharmaceutical composition is an oral dosage form that is not enterically protected. In certain embodiments, the pharmaceutical composition comprises crofelemer, or other proanthocyanidin polymer composition from C. lechleri, in an aqueous formulation, either as enteric coated beads, granules or powder, or as a non-enteric coated formulation in a pharmaceutically acceptable aqueous carrier.

The pharmaceutical compositions described herein may further comprise excipients, for example, one or more of a diluting agent, binding agent, lubricating agent, disintegrating agent, coloring agent, flavoring agent or sweetening agent. Compositions may be formulated for selected coated and uncoated tablets, hard and soft gelatin capsules, sugar-coated pills, lozenges, wafer sheets, pellets and powders in sealed packet. For example, compositions may be formulated for topical use, for example, ointments, pomades, creams, gels and lotions.

In certain embodiments, these pharmaceutical compositions are suitable for topical or oral administration to a subject. In other embodiments, as described in detail below, the pharmaceutical compositions may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

A pharmaceutical carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing crofelemer include those suitable for oral, nasal, topical (including buccal and sublingual), rectal, vaginal, aerosol and/or parenteral administration. The compositions may conveniently be presented in unit dosage form and may be prepared by any methods known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.01% to about 99% of active ingredient, for example, from about 5% to about 70%, or from about 10% to about 30%.

Liquid dosage forms for oral or rectal administration of crofelemer may include, for example, pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to crofelemer may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Dosage forms for the topical or transdermal administration of crofelemer can include, for example, powders, sprays, ointments, pastes, creams, lotions, gels, solutions, patches and inhalants. The ointments, pastes, creams and gels may contain, in addition to crofelemer, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a crofelemer, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Examples of suitable aqueous and non-aqueous carriers which may be employed in the pharmaceutical compositions can include, for example, water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In one embodiment, crofelemer is enteric coated so as to protect it from degradation by the acidic conditions of the stomach and/or from interactions with proteins, such as pepsin, present in the stomach, e.g., an enteric protected formulation. In a specific embodiment, crofelemer is in tablet form. In yet another embodiment, the tablet is enteric coated, e.g., Eudragit®. In one embodiment, crofelemer is formulated as an enteric coated bead or granule in an enteric coated capsule shell. In another embodiment, crofelemer is formulated in a delayed release composition.

In certain embodiments, the composition is formulated with a compound or compounds which neutralize stomach acid. Alternatively, the pharmaceutical composition containing the composition is administered either concurrent with or subsequent to or after administration of a pharmaceutical composition which neutralize stomach acid. Compounds, such as antacids, which are useful for neutralizing stomach acid include, but are not limited to, aluminum carbonate, aluminum hydroxide, bismuth subnitrate, bismuth subsalicylate, calcium carbonate, dihydroxyaluminum sodium carbonate, magaldrate, magnesium carbonate, magnesium hydroxide, magnesium oxide, and mixtures thereof. Compounds that are able to reduce the secretion of stomach acid and/or are able to reduce the acidity of stomach fluid are well known in the art and include, but are not limited to, antacids (aluminum hydroxide, aluminum carbonate, aluminum glycinate, magnesium oxide, magnesium hydroxide, magnesium carbonate, calcium carbonate, sodium bicarbonate), stomach acid blockers and a combination of any of the foregoing. In general, any drug that has been approved for sale by the relevant government agency and is able to reduce the production of stomach acid and/or reduce the acidity of stomach fluid can be administered in combination with an inhibitor molecule, such as crofelemer, in accordance with the methods presented herein.

In a particular embodiment where crofelemer is not enteric coated, crofelemer is formulated with one or more compounds that are able to reduce the secretion of stomach acid and/or able to reduce the acidity of stomach fluid. In an exemplary embodiment, crofelemer is formulated in a controlled release (delayed release) composition, such as Merck GEM, Alza OROS, wax matrix (release is primarily delayed until after the formulation passes out of the stomach and into the intestine).

Also provided herein are pharmaceutical formulations of crofelemer comprising the composition along with a pharmaceutically acceptable carrier, at a dose which is therapeutically effective at treating SBS, bile acid diarrhea, or diarrhea associated with a cholecystectomy or a small intestine resection. In one embodiment, a directly compressible crofelemer (e.g., that can be directly compressed, without excipients, into a tablet of pharmaceutically acceptable hardness and friability) compressed into a tablet, optionally with a lubricant, such as but not limited to magnesium stearate, is enteric coated. These formulations can be prepared by methods known in the art, see, e.g. methods described in Remington's Pharmaceutical Sciences, 18th Ed., ed. Alfonso R. Gennaro, Mack Publishing Co., Easton, Pa., 1990.

In a specific embodiment, the proanthocyanidin polymer composition comprises crofelemer (CAS 148465-45-6).

In a more another embodiment, a composition is enteric coated. Enteric coatings are those coatings that remain intact in the stomach, but will dissolve and release the contents of the dosage form once it reaches the small intestine. A large number of enteric coatings are prepared with ingredients that have acidic groups such that, at the very low pH present in the stomach, i.e. pH 1.5 to 2.5, the acidic groups are not ionized and the coating remains in an undissociated, insoluble form. At higher pH levels, such as in the environment of the intestine, the enteric coating is converted to an ionized form, which can be dissolved to release the inhibitor molecule. Other enteric coatings remain intact until they are degraded by enzymes in the small intestine, and others break apart after a defined exposure to moisture, such that the coatings remain intact until after passage into the small intestines.

Polymers which are useful for the preparation of enteric coatings include, but are not limited to, shellac, starch and amylose acetate phthalates, styrene-maleic acid copolymers, cellulose acetate succinate, cellulose acetate phthalate (CAP), polyvinylacetate phthalate (PVAP), hydroxypropylmethylcellulose phthalate (grades HP-50 and HP-55), ethylcellulose, fats, butyl stearate, and methacrylic acid-methacrylic acid ester copolymers with acid ionizable groups. In one embodiment, the pharmaceutical composition contains a polymeric proanthocyanidin composition and the enteric coating polymer Eudragit® L 30D, an anionic copolymer of methacrylic acid and methyl acrylate with a mean molecular weight of 250,000 Daltons. In another embodiment, the enteric coating polymer is Eudragit® L 30D-55. Application of the enteric coating to the crofelemer composition can be accomplished by any method known in the art for applying enteric coatings. For example, but not by way of limitation, the enteric polymers can be applied using organic solvent based solutions containing from 5 to 10% w/w polymer for spray applications and up to 30% w/w polymer for pan coatings. Solvents that are commonly in use include, but are not limited to, acetone, acetone/ethyl acetate mixtures, methylene chloride/methanol mixtures, and tertiary mixtures containing these solvents. Some enteric polymers, such as methacrylic acid-methacrylic acid ester copolymers can be applied using water as a dispersant. The volatility of the solvent system must be tailored to prevent sticking due to tackiness and to prevent high porosity of the coating due to premature spray drying or precipitation of the polymer as the solvent evaporates.

In another embodiment, the pharmaceutical composition comprising crofelemer is formulated as enteric coated granules or powder (microspheres with a diameter of 300-5001) provided in either hard shell gelatin capsules or suspended in an oral solution for pediatric administration. The enteric coated powder or granules may also be mixed with food, particularly for pediatric administration.

The granules and powder can be prepared using any method known in the art, such as but not limited to, crystallization, spray-drying or any method of comminution, for example, using a high speed mixer/granulator. Exemplary formulations may be found, for example, in the following US patents and applications U.S. Pat. No. 7,341, 744; U.S. Ser. No. 11/510,152; and U.S. Ser. No. 12/175, 131.

In other embodiments, the pharmaceutical composition comprising crofelemer is an aqueous formulation of crofelemer without any enteric coating or protection in a pharmaceutically acceptable aqueous vehicle.

Regardless of the route of administration selected, crofelemer is formulated into pharmaceutically-acceptable dosage forms by methods known to those of skill in the art.

In combination therapy treatment, both the compounds and the other drug agent(s) are administered to mammals (e.g., humans, male or female) by methods known in the art. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment in which another therapeutic agent is administered to an animal, the effective amount of the compound is less than its effective amount in case the other therapeutic agent is not administered. In another embodiment, the effective amount of the agent is less than its effective amount in case the compound is not administered. In this way, undesired side effects associated with high doses of either agent may be minimized. Other potential advantages (including without limitation improved dosing regimens and/or reduced drug cost) will be apparent to those skilled in the art.

In various embodiments, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In one or more embodiments, two or more therapies are administered within the same patient's visit.

V. KITS

Kits are also provided herein, for example, kits for treating SBS, bile acid diarrhea, or diarrhea associated with a cholecystectomy or a small intestine resection in a subject. The kits may contain, for example, crofelemer or a pharmaceutical composition comprising crofelemer and instructions for use. The instructions for use may contain prescribing information, dosage information, storage information, and the like.

Label instructions include, for example, instructions to take the crofelemer for at least 3 days for the treatment of SBS, bile acid diarrhea, or diarrhea associated with a cholecystectomy or a small intestine resection. The instructions could also read, for example, take from between 125 mg daily or 125 mg BID to 500 mg BID of crofelemer until resolution of symptoms. The instructions could also read, for example, take 500 mg BID of crofelemer until resolution of symptoms of SBS, bile acid diarrhea, or diarrhea associated with a cholecystectomy or a small intestine resection.

VI. EXAMPLES

Example 1

A female patient, 67 years of age, had an unresectable Desmoid tumor in the retroperitoneum which invaded the mesentery of the colon and small bowel. This necessitated the formation of a small bowel ostomy, leading to the development of SBS.

As a result, the patient suffered from chronic diarrhea. For 12 years, the patient attempted to treat the diarrhea with loperamide, diphenoxylate and/or atropine, codeine, or opium tincture. None of which were effective in relieving her symptoms.

The patient started taking crofelemer at 125 mg BID and her symptoms improved. The patient continued taking crofelemer at 125 mg BID for a year with the same level of effectiveness. The patient briefly discontinued taking crofelemer after a year, and the diarrhea symptoms resumed.

Example 2

A female patient 57 years of age had a laparoscopic cholecystectomy and immediately following the procedure experienced watery diarrhea with a frequency of about 10-12 watery diarrhea movements per week. Administration of probiotics and OTC anti-diarrheal medication were not effective.

Approximately three years post-surgery, as the patient was still experiencing watery diarrhea at a frequency of about 10-12 watery diarrhea movements per week, the patient began taking crofelemer. The patient received 125 mg BID of crofelemer for several weeks until the bowel movements normalized and then began taking 125 mg of crofelemer daily thereafter. For the first 6 weeks on 125 mg of crofelemer daily, the patient reported normal bowel movements and no episodes of diarrhea.

All publications, patents, and patent applications cited herein are hereby incorporated herein by reference in their entirety.

What is claimed is:

1. A method of treating short bowel syndrome (SBS) or secretory diarrhea associated therewith in a subject comprising administering to a subject in need thereof an amount of proanthocyanidin polymer composition from *C. lechleri* effective to treat SBS or secretory diarrhea associated therewith.

2. The method of claim 1, wherein the SBS results from surgical resection of the intestine.

3. The method of claim 1, wherein the SBS is due to a congenital deficiency.

4. The method of claim 1, wherein the subject is an infant.

5. The method of claim 4, wherein the subject suffers from necrotizing enterocolitis.

6. The method of claim 5, wherein the subject suffers from intestinal anomalies, midgut volvulus, intestinal atresia, abdominal wall defect, malrotation, or long segment Hirschsprung's disease.

7. The method of claim 4, wherein, the subject to be treated is an infant within 1 week of birth, within 2 weeks of birth, within 1 month of birth, or within 6 months of birth.

8. The method of claim 4, wherein the infant is premature or was born prematurely.

9. The method of claim 1 wherein the subject to be treated is a non-infant juvenile or adult.

10. The method of claim 1, in which a portion of the large intestine or colon is also resected.

11. The method of claim 10, wherein the subject does not have all or a portion of the duodenum, the jejunum or the ileum, or a combination thereof.

12. The method of claim 1, wherein the subject is administered parenteral nutrition.

13. The method of claim 1, wherein the administration results in improvement in a hepatic and/or biliary disorder associated with the SBS and/or results in a reduction in the risk or incidence of liver failure or wherein the administration results in an improvement in hypotension, metabolic bone disease, small bowel bacterial overgrowth, enteric hyperoxaluria, D-lactic acidosis, risk of infection and/or wound healing.

\* \* \* \* \*